United States Patent
Masuyama et al.

(10) Patent No.: US 10,751,473 B2
(45) Date of Patent: Aug. 25, 2020

(54) GASKET, AND MEDICAL SYRINGE

(71) Applicant: SUMITOMO RUBBER INDUSTRIES, LTD., Kobe-shi, Hyogo (JP)

(72) Inventors: Yoshikazu Masuyama, Kobe (JP); Hiroaki Nakano, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 776 days.

(21) Appl. No.: 15/461,141

(22) Filed: Mar. 16, 2017

(65) Prior Publication Data
US 2017/0296752 A1    Oct. 19, 2017

(30) Foreign Application Priority Data

Apr. 15, 2016  (JP) .................................. 2016-082321

(51) Int. Cl.
*A61M 5/31*  (2006.01)
*A61M 5/315*  (2006.01)

(52) U.S. Cl.
CPC ...... *A61M 5/3135* (2013.01); *A61M 5/31513* (2013.01); *A61M 2005/3131* (2013.01); *A61M 2205/0216* (2013.01)

(58) Field of Classification Search
CPC .............. A61M 5/315; A61M 5/31513; A61M 5/31511; A61M 2005/3131; A61M 2205/0216; A61M 5/178; A61M 5/31
See application file for complete search history.

(56) References Cited

U.S. PATENT DOCUMENTS

| 4,303,070 | A | * | 12/1981 | Ichikawa | ......... A61M 5/31513 604/222 |
| 6,090,081 | A | | 7/2000 | Sudo et al. | |
| 8,960,685 | B2 | * | 2/2015 | Maeda | ............... A61M 5/31511 277/648 |

(Continued)

FOREIGN PATENT DOCUMENTS

| JP | 3-63344 U | 6/1991 |
| JP | 9-206377 A | 8/1997 |

(Continued)

OTHER PUBLICATIONS

Japanese Office Action, dated Jun. 11, 2020, for Japanese Application No. 2016-082321, along with an English translation.

*Primary Examiner* — Kevin C Sirmons
*Assistant Examiner* — Tezita Z Watts
(74) *Attorney, Agent, or Firm* — Birch, Stewart, Kolasch & Birch, LLP (57) ABSTRACT

A gasket (10) is used for a medical syringe (30), and includes a main body (11) made of an elastic material and an inert resin film (12) provided on a surface of the main body (11). The gasket (10) has a cylindrical shape, and includes a plurality of annular ribs (13, 14, 15) provided on an outer circumferential surface (20) thereof and each having a sliding contact portion (16) to be kept in sliding contact with an inner peripheral surface of a syringe barrel. The plurality of annular ribs are axially arranged from a distal end to a rear end of the gasket (10). The sliding contact portion (16) of a distal annular rib (13) has a width that is 1 to 25% of axial length of the cylindrical gasket.

16 Claims, 4 Drawing Sheets

(56) References Cited

U.S. PATENT DOCUMENTS

2004/0099994 A1     5/2004   Brinkhues
2016/0101239 A1     4/2016   Ishida et al.

FOREIGN PATENT DOCUMENTS

| JP | 2892617 | B2 | | 5/1999 | |
| JP | 3387775 | B2 | | 3/2003 | |
| JP | 4550365 | B2 | | 9/2010 | |
| JP | 2015-146871 | A | | 8/2015 | |
| WO | WO 02/092312 | A1 | | 11/2002 | |
| WO | WO-2009128265 | A1 | * | 10/2009 | ........ A61M 5/31513 |

* cited by examiner

GASKET, AND MEDICAL SYRINGE

TECHNICAL FIELD

The present invention relates to a gasket to be used for a medical syringe, and a medical syringe including the gasket.

BACKGROUND ART

In recent years, prefilled syringes including a syringe barrel preliminarily filled with a liquid drug are increasingly used, because they are easy to handle and prevent use of a wrong liquid drug. Since rubber members (e.g., a gasket and a nozzle cap) of such a prefilled syringe are kept in direct contact with the liquid drug until use, the gasket and the nozzle cap are generally made of a butyl rubber which is excellent in chemical resistance, gas barrier property, water vapor barrier property and anti-aging property.

However, some biological drugs are liable to be influenced by interaction with the rubber members and substances released from the rubber members. For improvement of the slidability of the gasket and prevention of the sticking of the nozzle cap, an inner wall of the syringe barrel and surfaces of the gasket and the nozzle cap made of the butyl rubber are often coated with a lubricant such as a silicone oil or a curable silicone. The silicon coating is liable to be separated from the barrel inner wall and the rubber members to significantly adversely influence some types of drugs.

To cope with this problem, rubber products laminated with a fluororesin film or the like to obviate the need for the silicone are developed for use in a glass syringe or a prefilled resin syringe.

A PTFE (polytetrafluoroethylene) film having an excellent chemical resistance and a minimum friction coefficient is suitable as the fluororesin film for the lamination of the gasket. Where the use of the silicone lubricant is permitted, an ETFE (ethylene tetrafluoroethylene) film may be used for the lamination. The PTFE film is typically produced by a skiving method, a casting method or the like.

A gasket having a fluororesin film provided on a liquid contact surface thereof and a slidable seal portion thereof to be kept in contact with the inner wall of the syringe barrel has problems associated with gas tightness and sliding resistance. Particularly, the film produced by the skiving method is liable to cause the problem associated with the gas tightness with respect to the inner wall of the syringe barrel because of its greater surface roughness.

Factors relevant to deterioration of the gas tightness are the smoothness (surface roughness) of the film used for the lamination, and variations in the inner diameter of the syringe barrel which influence the compression percentage of the gasket with respect to the inner diameter of the syringe barrel. The resin syringe barrel has a highly accurate inner diameter with a tolerance of ±0.1 mm. On the other hand, a material tube for the glass syringe barrel has greater variations in inner diameter, and even a glass syringe barrel having a volume of not greater than 5 mL has a relatively great inner diameter tolerance of ±0.15 mm.

Even if a PTFE film having a surface roughness Ra of not greater than 0.05 µm is used for the lamination, liquid leakage often occurs. This is because, even if the PTFE film is lamination-molded at a molding temperature of 170° C. (which is lower than the melting point (230° C.) of the PTFE), minute undulations of a mold surface are transferred to the surface of the lamination film to thereby influence the sealability.

To solve the problems associated with the gas tightness and the sliding resistance, there are proposed a gasket having a cylindrical drum shape (e.g., Patent Document 1), and a gasket having a plurality of annular ribs provided on a circumferential surface of a cylindrical gasket body (see, for example, Patent Document 2 and FIG. 3(e) in Patent Document 3).

CITATION LIST

Patent Document

[PATENT DOCUMENT 1] JP-HEI9(1997)-206377A
[PATENT DOCUMENT 2] JP-4550365B
[PATENT DOCUMENT 3] JP-3387775B

SUMMARY OF THE INVENTION

Problem to be Solved by the Invention

The conventional gasket configurations are still problematic in gas tightness and sliding resistance.

It is therefore a principal object of the present invention to provide a gasket laminated with an inert resin film and having a reduced sliding resistance and a higher liquid sealability.

Solution to Problem

According to the present invention, there is provided a gasket to be used for a medical syringe, the gasket including a main body made of an elastic material and an inert resin film provided on a surface of the main body. The gasket has a short cylindrical shape, and includes a plurality of annular ribs provided on an outer circumferential surface thereof and each having a sliding contact portion to be kept in sliding contact with an inner peripheral surface of a syringe barrel of the medical syringe. The plurality of annular ribs are axially arrange from a distal end to a rear end of the gasket. The sliding contact portion of a distal one of the annular ribs has a width that is 1 to 25% of the length of the outer circumferential surface of the cylindrical gasket as measured axially of the gasket.

In the present invention, the distal annular rib preferably has at least one annular groove formed in the sliding contact portion thereof as extending circumferentially of the gasket by laser processing.

The distal annular rib preferably has projections respectively projecting from opposite edges of the annular groove and each having a height of 2 to 100 µm as measured from an unprocessed portion of the sliding contact portion thereof.

The annular groove preferably has a groove width of not greater than 200 µm.

Effects of the Invention

According to the present invention, the sliding contact portion of the distal annular rib reliably seals a liquid drug, and has a lower sliding resistance. Thus, the gasket is excellent in both sealability and operability.

Further, the provision of the annular groove further improves the sealability of the gasket with the projections formed along the opposite edges of the annular groove.

EMBODIMENTS OF THE INVENTION

With reference to the attached drawings, one embodiment of the present invention will hereinafter be described specifically.

Figure 1:
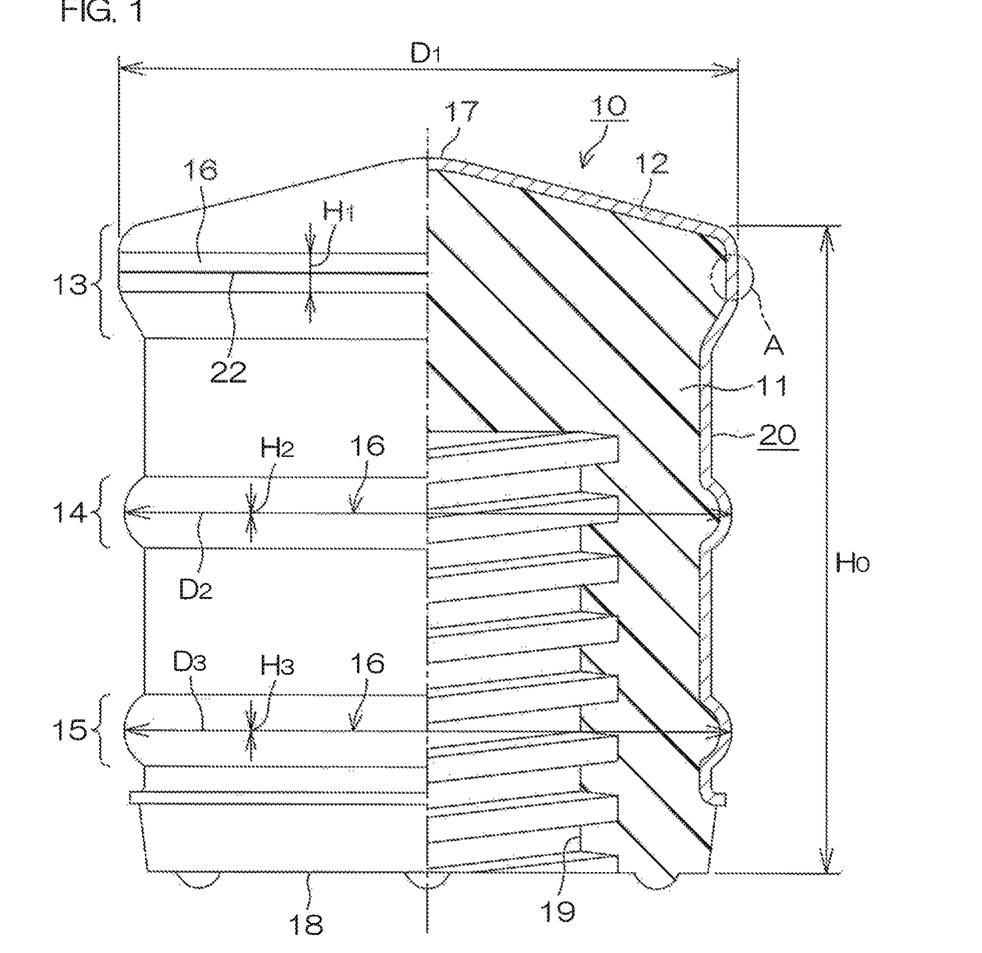
FIG. 1 is a front view of a gasket according to one embodiment of the present invention with a half of the gasket illustrated in section.

FIG. 1 is a front view of a gasket 10 according to the embodiment of the present invention with a right half of the gasket illustrated in section.

Referring to FIG. 1, the gasket 10 according to the embodiment of the present invention includes a main body 11 made of an elastic material, and an inert resin film 12 provided on a surface of the main body 11. The elastic material for the main body 11 is a rubber material. Examples of the rubber material include synthetic rubbers, thermoplastic elastomers, and materials prepared by blending any of the synthetic rubbers and the thermoplastic elastomers. More specifically, the rubber material may be prepared by using a butyl rubber, a halogenated butyl rubber, a styrene butadiene rubber, a butadiene rubber, an epichlorohydrin rubber, a neoprene rubber, an ethylene propylene rubber and/or the like.

The type of the inert resin film 12 provided on the surface of the main body 11 is not particularly limited, as long as the inert resin film is capable of preventing migration of substances from the main body 11 and has more excellent slidability, i.e., a smaller friction coefficient, than the rubber. Examples of the inert resin film include films of ultrahigh molecular weight polyethylenes and fluororesins which are proved to be practical in medical applications. Specific examples of the inert resin film include the following three types of inert films:
(1) A PTFE (polytetrafluoroethylene) homopolymer film produced by the skiving method (e.g., VALFLON (trade name) available from Nippon Valqua Industries, Ltd.);
(2) A modified PTFE (a copolymer of a tetrafluoroethylene monomer and several percents of a perfluoroalkoxide monomer) film produced by the skiving method (e.g., NEW VALFLON (trade name) available from Nippon Valqua Industries, Ltd.); and
(3) An ultrahigh molecular weight polyethylene film produced by the skiving method (e.g., NEW LIGHT NL-W (trade name) available from Saxin Corporation).

Referring again to FIG. 1, the gasket 10 has a short cylindrical shape, and its distal face 17 has a conical center portion, for example, axially projecting at an obtuse angle. The gasket 10 has a rear end face 18 axially recessed into an engagement recess 19 shaped in a female screw. A head of a plunger to be used for operating the gasket 10 is screwed into the engagement recess 19 of the gasket 10.

Three annular ribs 13, 14, 15 to be kept in sliding contact with an inner peripheral surface of a syringe barrel are provided on an outer circumferential surface (sliding surface) 20 of the cylindrical gasket 10, and arranged from the side of the distal end face 17 to the side of the rear end face 18 of the gasket 10 in axially spaced relation. Of these annular ribs, a distal annular rib 13 has a sliding contact portion 16 to be kept in sliding contact with the inner peripheral surface of the syringe barrel. The sliding contact portion 16 has a width $H_1$ that is 1 to 25% of the length $H_0$ of the outer circumferential surface 20 of the cylindrical gasket 10 as measured axially of the gasket 10.

That is, the following dimensional relationship is satisfied:

$$H_1 : H_0 = (1 \text{ to } 25) : 100$$

This is a feature of this embodiment.

As seen axially of the gasket 10, a second annular rib (middle annular rib) 14 is disposed below the distal annular rib 13, and a third annular rib (proximal annular rib) 15 is disposed below the second annular rib 14. In this embodiment, the middle annular rib 14 and the proximal annular rib 15 each have an arcuately bulged shape as seen in section. The sliding contact portions 16 of the middle annular rib 14 and the proximal annular rib 15 to be kept in sliding contact with the inner peripheral surface of the syringe barrel each have no width as measured axially of the gasket and, therefore, are slidable substantially in line contact with the inner peripheral surface of the syringe barrel.

Generally speaking, the sliding contact portions 16 of the annular ribs other than the distal annular rib 13, i.e., the middle annular rib 14 and the proximal annular rib 15, respectively have widths $H_2$ and $H_3$ that are 0 to 15% of the length $H_0$ of the outer circumferential surface 20 as measured axially of the gasket 10.

That is, the following dimensional relationships are desirably satisfied:

$$H_2 : H_0 = (0 \text{ to } 15) : 100$$

$$H_3 : H_0 = (0 \text{ to } 15) : 100$$

Further, the gasket 10 is configured so that the diameter $D_1$ of the distal annular rib 13, the diameter $D_2$ of the middle annular rib 14 and the diameter $D_3$ of the proximal annular rib 15 satisfy the following relationships:

$$D_1 > D_2$$

$$D_1 > D_3$$

The distal annular rib 13 has a radial compression percentage of 1 to 8%, and the middle annular rib 14 and the proximal annular rib 15 each have a slightly smaller radial compression percentage than the distal annular rib 13. The compression percentages of the distal annular rib 13, the middle annular rib 14 and the proximal annular rib 15 may be controlled by properly setting the inner diameter of the engagement recess 19 of the main body 11 and the like.

In this embodiment, two annular ribs, i.e., the middle annular rib 14 and the proximal annular rib 15, are provided in addition to the distal annular rib 13 byway of example. The number of the annular ribs other than the distal annular rib 13 is not limited to two, but may be one or not less than three.

Figure 2:
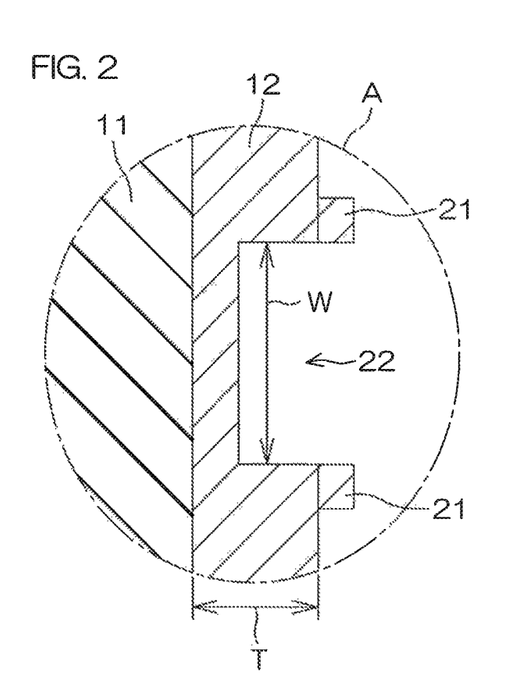
FIG. 2 is an enlarged view of a portion A shown in FIG. 1.

FIG. 2 is an enlarged view of a portion A shown in FIG. 1.

Referring to FIGS. 1 and 2, the sliding contact portion 16 of the distal annular rib 13 desirably has at least one annular groove 22 formed as extending circumferentially thereof by laser processing.

Referring to FIG. 2, the annular groove 22 will be described more specifically.

The groove 22 is provided in a surface of the inert resin film 12, and the main body 11 is not recessed correspondingly to the groove 22. That is, the groove 22 exerts no influence on the shape of the main body 11, but is present only in the inert resin film 12.

A part of the inert resin film 12 formed with the groove 22 has a thickness smaller than the thickness T of the inert resin film 12 not formed with the groove 22.

The groove 22 desirably has a width W of not greater than 200 μm, preferably not greater than 100 μm, more preferably not greater than 50 μm.

Portions of the inert resin film 12 present along opposite edges of the groove 22 are respectively formed with projections 21 and, therefore, are slightly thicker than the original thickness T of the inert resin film 12. The formation of the projections 21 is achieved when the groove 22 is formed by the processing with a laser beam. A surface portion of the inert resin film 12 is evaporated or decomposed by the laser beam, and the film material is partly re-deposited along the opposite edges of the groove 22 to form the projections 21.

The projections 21 desirably each have a height of 2 to 100 μm to locally provide proper surface pressures.

Figure 3:
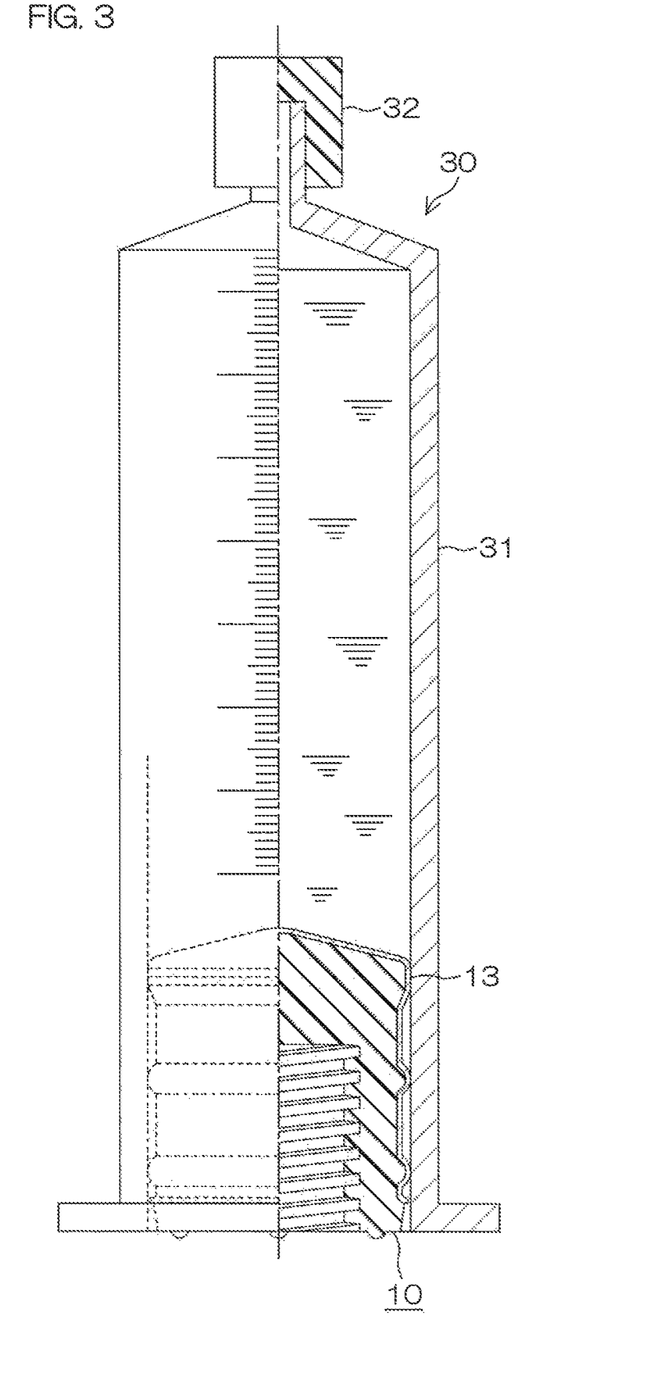
FIG. 3 is a front view of an exemplary medical syringe incorporating the gasket of the embodiment of the present invention with a half of the syringe illustrated in section.

FIG. 3 is a front view of an exemplary medical syringe (prefilled syringe) incorporating the gasket 10 of the embodiment of the present invention with a half of the syringe illustrated in section.

The prefilled syringe 30 includes a hollow cylindrical syringe barrel 31, a sealing cap 32 attached to a distal end of the syringe barrel 31, and the gasket 10 inserted into the syringe barrel 31 from a rear end of the syringe barrel 31. The syringe barrel 31 is filled with a predetermined liquid drug.

For use, the sealing cap 32 is removed from the distal end of the syringe barrel 31, and an injection needle is attached to the distal end. Then, a plunger (not shown) is threadedly engaged with the gasket 10 from the rear end face of the gasket 10, and operated to slide the gasket 10, whereby the liquid drug in the syringe barrel 31 is administered through the injection needle.

With this arrangement, the distal annular rib 13 of the gasket 10 is capable of properly sealing the liquid drug, and has a relatively small sliding resistance. Therefore, the medical syringe 30 is excellent in slidability, operability, and sealability (gas tightness and liquid tightness).

EXAMPLES

Figure 4:
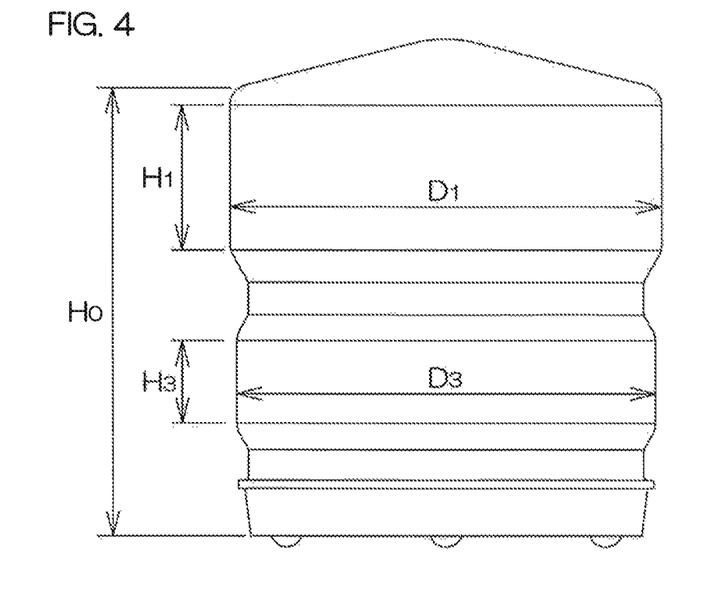
FIG. 4 is a diagram showing an appearance of a conventional gasket.

Gaskets of Examples 1 to 3 and Comparative Example 2 were produced as each having a configuration shown in FIG. 1, and a gasket of Comparative Example 1 was produced as having a configuration shown in FIG. 4. Materials used for the production of the gaskets are as follows:

(1) Material for Main Body 11

A chlorinated butyl rubber material (having a JIS-A hardness of 58 degrees)

(2) Material for Inert Resin Film 12

A modified PTFE film produced by the skiving method and having a film thickness T of 70 μm and a center-line average surface roughness of 0.11 μm (NEW VALFLON (trade name) available from Nippon Valqua Industries, Ltd.)

(3) Production Method

A PTFE film produced by the skiving method as having a thickness of 70 μm and having a surface treated for adhesion was stacked on an unvulcanized rubber sheet of the fluorinated butyl rubber. Then, the resulting stack was put on a mold, and vulcanization-molded at 175° C. for 10 minutes by means of a vacuum press, whereby the PTFE film was bonded to the rubber sheet.

The gaskets were each configured so as to be fitted in a 1-mL COP resin syringe (including a syringe barrel having an inner diameter of 6.35 mm).

(4) Laser Beam Processing

The gaskets were each processed by a laser beam to be thereby formed with an annular groove 22.

A 3-Axis $CO_2$ Laser Marker ML-Z9550T available from Keyence Corporation was used as an apparatus for the laser processing. The formation of the annular groove 22 was achieved by applying a laser beam having a wavelength of 9300 nm.

(5) The gaskets of Examples and Comparative Examples were configured and dimensioned as follows.

Example 1

Number of annular ribs: 3
$H_0$: 7.0 mm
$D_1$: 6.65 mm
$H_1$: 1.0 mm
$D_2$: 6.6 mm
$H_2$: 1.0 mm
$D_3$: 6.6 mm
$H_3$: 1.0 mm
Annular groove 22: Absent Example 2

Number of annular ribs: 3
$H_0$: 7.0 mm
$D_1$: 6.6 mm
$H_1$: 1.5 mm
$D_2$: 6.55 mm
$H_2$: 0.5 mm
$D_3$: 6.55 mm
$H_3$: 0.5 mm
Annular groove 22: Present Example 3

Number of annular ribs: 3
$H_0$: 7.0 mm
$D_1$: 6.7 mm
$H_1$: 0.5 mm
$D_2$: 6.55 mm
$H_2$: 0 mm
$D_3$: 6.55 mm
$H_3$: 0 mm
Annular groove 22: Present Comparative Example 1

Number of annular ribs: 2
$H_0$: 7.0 mm
$D_1$: 6.6 mm
$H_1$: 3.0 mm
$D_3$: 6.6 mm
$H_3$: 2.0 mm
Annular groove 22: Absent Comparative Example 2

Number of annular ribs: 3
$H_0$: 7.0 mm
$D_1$: 6.6 mm
$H_1$: 1.5 mm
$D_2$: 6.6 mm
$H_2$: 1.0 mm $D_3$: 6.6 mm
$H_3$: 1.0 mm
Annular groove 22: Absent
<Test Methods>
(1) Slidability The processed gasket products were each inserted into a syringe barrel, and a force required for squeezing the gasket at a speed of 100 mm/min in the syringe barrel by a plunger was measured by means of a precision universal tester (AG-X 100 kN available from Shimadzu Corporation). An average force required for sliding the gasket product for a sliding distance of 10 mm to 15 mm was determined, and recorded as a sliding resistance.

(2) Liquid Drug Sealability

The gasket products thus produced were each inserted into a syringe barrel, which was in turn filled with a test liquid. Then, an opposite end of the syringe barrel was capped. The resulting syringe barrel was allowed to stand still at 40° C. for one week, and then observed with an objective lens having a magnification of 50× by means of a video microscope (DVM5000 available from Leica Microsystems Inc.) to be checked for liquid leakage. For each of the gasket products, 20 samples were observed, and the number of samples suffering from liquid leakage (in which the test liquid penetrated beyond the maximum diameter portion $D_1$ of the gasket product) was recorded. A gasket product with two or less samples suffering from the liquid leakage was rated as acceptable. The test liquid herein used was prepared by adding 0.2 g/liter of a colorant (Methylene Blue available from Sigma Aldrich Japan LLC.) and 1.0 g/liter of a surfactant (POLYSORBATE 80 available from NOF Corporation) to water. The syringe barrel was made of a cycloolefin resin, and had an inner diameter of 6.35 mm.

<Comprehensive Evaluation>

The results of comprehensive evaluation are shown in Table 1, and evaluation criteria are shown in Table 2.

TABLE 2

|  | Evaluation criteria | Sliding resistance |
|---|---|---|
| Slidability | ⊚ (Excellent) | Less than 7N |
|  | ○ (Acceptable) | 7 to 10N |
|  | Δ (Unacceptable) | Greater than 10N |

This application corresponds to Japanese Patent Application No. 2016-082321 filed in the Japan Patent Office on Apr. 15, 2016, the disclosure of which is incorporated herein by reference in its entirety.

What is claimed is:

1. A gasket to be used for a medical syringe, the gasket comprising:
   a main body made of an elastic material; and
   an inert resin film provided on a surface of the main body;
   the gasket having a cylindrical shape, and including a plurality of annular ribs provided on an outer circumferential surface thereof and each of the plurality of annular ribs having a sliding contact portion to be kept in sliding contact with an inner peripheral surface of a syringe barrel of the medical syringe, the plurality of annular ribs being axially arranged from a distal end to a rear end of the gasket;
wherein
   the sliding contact portion of a distal annular rib of the plurality of annular ribs has a width that is 1 to 25% of the cylindrical gasket axial length,
   the distal annular rib has a radial compression percentage of 1 to 8%,
   the distal annular rib has at least one annular groove formed in the sliding contact portion thereof, the at least one annular groove extending circumferentially of the gasket, and
   the at least one annular groove is formed by laser processing.

TABLE 1

|  | Example 1 | Example 2 | Example 3 | Comparative Example 1 | Comparative Example 2 |
|---|---|---|---|---|---|
| Gasket configuration |  |  |  |  |  |
| Number of annular ribs | 3 | 3 | 3 | 2 | 3 |
| Linear length of sliding contact portion $H_0$ (mm) | 7.0 | 7.0 | 7.0 | 7.0 | 7.0 |
| Distal rib |  |  |  |  |  |
| Rib diameter $D_1$ (mm) | 6.65 | 6.6 | 6.7 | 6.6 | 6.6 |
| Compression percentage (%) | 4.5 | 3.8 | 5.2 | 3.8 | 3.8 |
| Width $H_1$ (mm) | 1.0 | 1.5 | 0.5 | 3.0 | 1.5 |
| Percentage (%) | 14.3 | 21.4 | 7.1 | 42.9 | 21.4 |
| Middle rib |  |  |  |  |  |
| Rib diameter $D_2$ (mm) | 6.6 | 6.55 | 6.55 | — | 6.6 |
| Compression percentage (%) | 3.8 | 3.1 | 3.1 | — | 3.8 |
| Width $H_2$ (mm) | 1.0 | 0.5 | 0 | — | 1.0 |
| Percentage (%) | 14.3 | 7.1 | 0 | — | 14.3 |
| Proximal rib |  |  |  |  |  |
| Rib diameter $D_3$ (mm) | 6.6 | 6.55 | 6.55 | 6.6 | 6.6 |
| Compression percentage (%) | 3.8 | 3.1 | 3.1 | 3.8 | 3.8 |
| Width $H_3$ (mm) | 1.0 | 0.5 | 0 | 2.0 | 1.0 |
| Percentage (%) | 14.3 | 7.1 | 0 | 28.5 | 14.3 |
| Groove | Absent | Present | Present | Absent | Absent |
| Slidability | ○ | ○ | ⊚ | Δ | ○ |
| Liquid drug sealability (occurrence of liquid leakage) | 0/10 | 0/10 | 0/10 | 0/10 | 4/10 |

2. The gasket according to claim 1, wherein the distal annular rib has projections respectively projecting from opposite edges of the at least one annular groove and each having a height of 2 to 100 µm.

3. The gasket according to claim 2, wherein the annular groove has a groove width of not greater than 200 µm.

4. The gasket according to claim 1, wherein the sliding contact portion of each of the plurality of annular ribs other than the distal annular rib has a width that is 1 to 15% of the cylindrical gasket axial length.

5. The gasket according to claim 1, wherein the sliding contact portion of each of the plurality of annular ribs other than the distal annular rib has a width that is 1 to 15% of the cylindrical gasket axial length.

6. The gasket according to claim 5, wherein the plurality of annular ribs other than the distal annular rib each have a smaller radial compression percentage than that of the distal annular rib.

7. The gasket according to claim 1, wherein the plurality of annular ribs other than the distal annular rib each have a smaller radial compression percentage than that of the distal annular rib.

8. The gasket according to claim 1, wherein the inert resin film is one of a polytetrafluoroethylene (PTFE) film, an ethylene tetrafluoroethylene copolymer (ETFE) film and an ultrahigh molecular weight polyethylene (UHWPE) film.

9. A medical syringe comprising a tubular syringe barrel, and a gasket fitted in the syringe barrel, wherein the gasket is the gasket according to claim 1.

10. A medical syringe comprising a tubular syringe barrel, and a gasket fitted in the syringe barrel, wherein the gasket is the gasket according to claim 2.

11. A medical syringe comprising a tubular syringe barrel, and a gasket fitted in the syringe barrel, wherein the gasket is the gasket according to claim 3.

12. A medical syringe comprising a tubular syringe barrel, and a gasket fitted in the syringe barrel, wherein the gasket is the gasket according to claim 4.

13. A medical syringe comprising a tubular syringe barrel, and a gasket fitted in the syringe barrel, wherein the gasket is the gasket according to claim 5.

14. A medical syringe comprising a tubular syringe barrel, and a gasket fitted in the syringe barrel, wherein the gasket is the gasket according to claim 7.

15. A medical syringe comprising a tubular syringe barrel, and a gasket fitted in the syringe barrel, wherein the gasket is the gasket according to claim 6.

16. A medical syringe comprising a tubular syringe barrel, and a gasket fitted in the syringe barrel, wherein the gasket is the gasket according to claim 8.

* * * * *